United States Patent [19]

Gordon

[11] Plant 4,144

[45] Nov. 8, 1977

[54] APPLE TREE

[76] Inventor: Robert B. Gordon, 8115 Ocean View Ave., Whittier, Calif. 90602

[21] Appl. No.: 736,955

[22] Filed: Oct. 29, 1976

[51] Int. Cl.[2] ..... A01H 5/03

[52] U.S. Cl. ..... Plt./34

[58] Field of Search ..... Plt./34

*Primary Examiner*—Robert E. Bagwill
*Attorney, Agent, or Firm*—Joseph F. Cuneo

[57] ABSTRACT

A new variety of apple tree that does extremely well in the mild climatic coastal regions of Southern California. The plant has a long flowering period that normally commences in the early part of April and extends through the month of May. The tree produces an abundance of green-red colored apples that range from medium to large in size, the flesh of the fruit is crisp, firm, fine textured and very juicy. The flavor of the apples is sweet-tart and the fruit has a distinct aroma making it excellent as eating apples; the fruit is also very good when made into sauce, baked or cooked in other ways. The first fruit normally starts to ripen by mid August and the tree continues to bear fruit until the middle of October.

1 Drawing Figure

The present invention relates to a new and distinct variety of apple tree which was discovered by me as a chance seedling of unknown parentage growing on my property located at 8115 Ocean View Ave., Whittier, Calif.

A distinguishing characteristic of this new variety of apple is its ability to produce apples of good eating quality, texture, and flavor in an area that is not ordinarily associated with the cold weather and chilling temperatures that are usually considered necessary for the raising of good quality apples. The region in which this variety of apple was discovered by me and in which it has been observed for many years, is classed as a mild climatic zone identified as the Whittier Hills Area. This is an area that has been very suitable for the production of avocados and some more tropical types of fruit. This is shown by the fact that I have been successfully producing fair sized edible bananas within fifty feet of the new variety of apple tree for over 20 years.

In addition to the new variety being able to produce apples of good quality, flavor, texture and aroma in abundant quantities in a warm weather locale, other important and distinguishing characteristics are the production of bright red and green colored fruit that range from medium to large in size and have a distinctive sweet-tart flavor. The flesh of the fruit is classed as tender yet it is firm and is quite juicy. The apples, when the fruit is mature, give off an aroma that is most appetizing. The apples also respond well to cooking and retain the sweet-tart flavor and aroma after having been converted into sauce, baked, or made into an apple pie. This is unusual since most apples fall into one or the other of the two categories, cooking or eating apples. This new variety may be used satisfactorily either as an eating apple or as a cooking apple.

Another unusual feature of this new variety is its long flowering and fruiting period. The flower illustration included in the drawings was taken on May 27, 1976, at the time when the opened flowers were about 2 weeks old. On a branch near to the one to which these flowers were attached and which also had open flowers attached to it there was an apple that had already attained a diameter of 2¼ inches. Flowering usually starts in early April and normally continues throughout the month of May; occasionally the flowering period will extend into the early portion of June. The flowers of the new variety are also different in that at the time the petals first open they are colored a deep deep pink. As the flowers progress toward maturity their color will change to a deep pink, then to a medium pink and just as the flowers become mature the color will become light pink. By the time the flowers are ready to fall from the branches the color will be almost white.

The first apples are usually ready to be picked by the middle of August in normal years, and apples can continue to be harvested until after the end of the first week in October. The dates of the first and last picking are normally about August 17 and October 10. It has been observed that ripe fruit continues to retain its bright color, firm tenderness, and its sweet-tart flavor and juiciness even after it has been left unpicked on the tree as long as three weeks after it has reached full maturity.

The new variety has been successfully reproduced asexually by budding and grafting. The resulting plants are rather fast growers. For example, several trees were reproduced by grafting at Visalia, Calif. on Mar. 3, 1976. The resulting plants were continuously observed and by June 7, 1976 the plant had attained a height of approximately 3 feet and a caliper of three eighths of an inch. By Aug. 7, 1976 the plants had reached an average height of 6 feet.

The following is a detailed description of this new variety, with color terminology in accord with the ordinary dictionary significance except where indicated to be in accord with the new RHS Colour Charts published by the Royal Horticultural Society, London, England, that were copyrighted in 1966.

Tree: Medium large size; vigorous; upright; dense upright growth; hardy; rapid growing; very productive; regular bearer.

*Trunk.*—Medium stocky; smooth.

*Branches.*—Medium stockiness; medium smooth; much branched. Color — Approximately RHS Colour Chart 199A; semi-glossy. Lenticels — numerous; medium size.

*Leaves.*—Length of mature leaf blade, exclusive of petiole, averages 4¼ inches with some leaves reaching a length of 6 inches. Width at widest point averages 2¼ to 2½ inches with the largest leaves being 3 inches in width. Nearly oval in shape often approaching an ovate shape with the apex acuminate and the base obtuse. Leaf is of medium thickness with the upper surface lightly rugose especially among veinlets. Upper surface is glabrous, under surface is tomentose with the veins being more prominent on the underside. Color — Mature; upper surface— RHS Colour Chart 139A; lower surface— RHS Colour Chart 138B. Margin — Serrate. Petiole — Length 1⅝ inches to 2⅛ inches; medium thickness. Color — RHS Colour Chart 139D.

*Flowers.*—When petals first open; Color — approximately RHS Colour Chart 52A. After flower petals have opened; Color — the pink color continues to grow lighter as the flower progresses to full maturity; by the time the flowers have reached full maturity the petals are slightly pinkish white. Date of first bloom — Early in April. Continuity — Ordinarily flowers continue to come out throughout the remainder of April and flowering will remain on the tree through May; occasionally some flowers will remain on the tree in the early part of June.

Fruit:

*Maturity when described.*—Eating ripe. Date — The first apples will be ripe by August 15 in normal years. Fully ripe fruit can be picked from the beginning of the third week of August up to the end of the second week of October; the fruiting season starts early and is of long duration.

*Size.*—Variable from medium to large. Diameter axial — 2½ inches to 4 inches. In transverse plane — 4 inches to 5 inches.

*Form.*—Slightly variable; nearly globose; truncate at base and apex making fruit wider than tall. In most fruit the axial height of the fruit is less at one end of the transverse diameter than at the opposite end. Base — Cavity is shallowly rounded. Apex — shallow depression with slightly rounded protuberance at the base of each sepal.

*Stem.*—Medium stout; strong adherence; length ¾ inches to 1 inch.

*Skin.*—Medium thick; smooth; medium tender. Color — Unripe fruit is uniform green color RHS Colour Chart between 145 B and 145 C. As ripening progresses very prominent vertical red stripes appear until red stripes are distributed substantially all around the apple, when fully mature the red color of the skin varies from RHS Colour Chart 42A to 42B with the red stripes becoming more solidly joined until they cover from 45% to 55% of the total skin surface.

*Flesh.*—Crisp; very juicy. Texture — Firm; crisp; fine textured. Color — Near white. Flavor — Sweet-tart. Aroma — Distinct, fruity apple bouquet. Eating quality — Excellent for eating. Cooking quality — Exceptionally good for apple sauce, pies, apple butter, clear apple jelly, and for baking.

*Seed.*—There are five seed cells in each apple. Number — There is one seed in each seed cell. Size — Length of seed is usually 5/16 of an inch; width at the widest point is 3/16 of an inch. Color — Medium brown.

Use: Market; local; home use, excellent either as an eating apple or as a cooking apple.

Keeping quality: Good.

I claim:

1. A new and distinct variety of apple tree substantially as shown and described, characterized as to novelty by the abundant production of medium to large size apples having a beautiful green and red coloring suitable for growing in the mild climatic coastal regions of Southern California, by the flesh of said apples which is crisp, firm, fine textured and very juicy and has a sweet-tart flavor and a distinct aroma making the apples excellent for both eating and cooking, by its long flowering period that commences early in April and continues throughout the month of May, by the deep deep pink color of the petals at the time the flowers first open, said deep pink color of the petals becoming progressively lighter pink as the flowers approach maturity and becoming a very pale pink at full maturity, by the early maturing of the fruit and by its long bearing season that provides ripe apples commencing in mid August and continuing until mid October, and by its vigorous, dense, upright growth habit that provides an attractive tree suitable for residential planting as well as for orchard use.

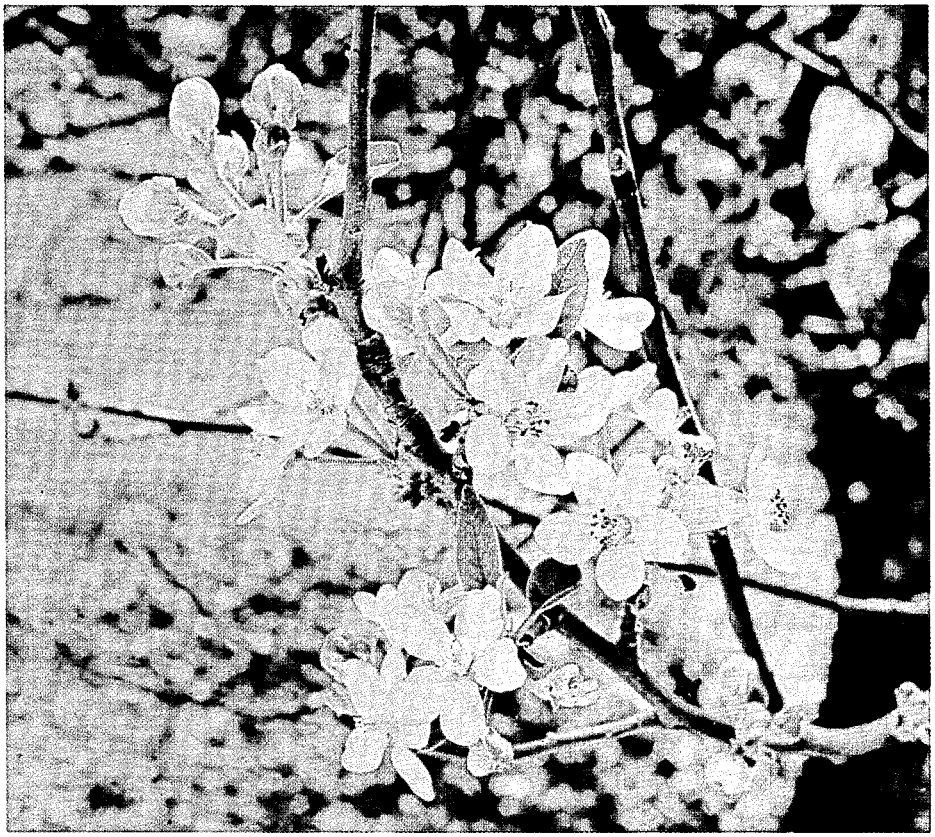
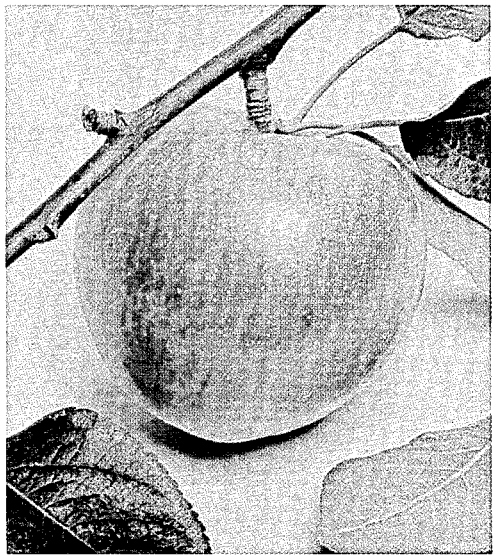
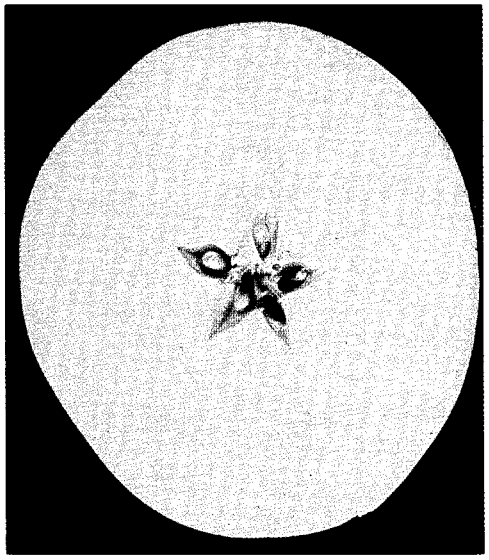

* * * * *